(12) United States Patent
Burns et al.

(10) Patent No.: US 6,361,979 B1
(45) Date of Patent: Mar. 26, 2002

(54) MICROBIAL CONVERSION OF 2-METHYLQUINOXALINE

(75) Inventors: Michael P. Burns, Mystic; James J. Cawley, Lyme; John W. Wong, East Lyme, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/492,548

(22) Filed: Jan. 27, 2000

Related U.S. Application Data

(60) Provisional application No. 60/119,942, filed on Feb. 12, 1999.

(51) Int. Cl.[7] ............ C12P 17/16; C12P 17/18; C12N 1/20; C12N 1/14
(52) U.S. Cl. ............ 435/119; 435/118; 435/120; 435/121; 435/122; 435/877; 435/911; 435/913; 435/933
(58) Field of Search ............ 435/118–122, 877, 435/911, 912, 913, 933

(56) References Cited

U.S. PATENT DOCUMENTS

| | | | |
|---|---|---|---|
| 4,859,592 A | 8/1989 | Hagedorn et al. | 435/122 |
| 5,104,798 A | 4/1992 | Kiener | 435/117 |
| 5,213,973 A | 5/1993 | Hoeks | 435/117 |
| 5,236,832 A | 8/1993 | Kiener | 435/117 |

OTHER PUBLICATIONS

Mounfield et al. The formation of 1–hydroxymethylnaphthalene and 6–hydroxymethylquinoline by both oxidative and reductive routes in Cunninghamella elegans. Appl. Microbiol. Biotechol. (1998) 50:379–383.*

Hamilton et al. Microbiological metabolism of naphthyridines. Appl. Microbiol. (1969). vol. 17, No. 2, pp. 237–241.*

Gaucher, G. M. et al., *Dev. Ind. Microbiol.*, vol. 22, pp. 219–232 (1981).

Harayama, S. et al., *J. Bacteriol.*, vol. 167 (2), pp. 455–461 (1986).

Keiner, A., *Angew. Chem. Int. Ed. Engl.*, vol. 31 (6), pp. 774–775 (1992).

* cited by examiner

Primary Examiner—Sandra E. Saucier
Assistant Examiner—Vera Afremova
(74) Attorney, Agent, or Firm—Peter C. Richardson; Gregg C. Benson; Jennifer A. Kispert

(57) ABSTRACT

The present invention relates to processes for the microbial oxidation of 2-methylquinoxaline to 2-quinoxalinecarboxylic acid which comprise contacting 2-methylquinoxaline with a microorganism, or a suitable mutant thereof, and incubating the resulting mixture under conditions sufficient to yield an amount of said 2-quinoxalinecarboxylic acid. The present processes optionally further comprise the isolation and purification of 2-quinoxalinecarboxylic acid.

37 Claims, No Drawings

MICROBIAL CONVERSION OF 2-METHYLQUINOXALINE

CROSSREFERENCE TO RELATED APPLICATION

This application claims priority from U.S. Provisional Patent Application No. 60/119,942 filed Feb. 12, 1999, the benefit of which is hereby claimed under 37 C.F.R. §1.78 (a)(3).

FIELD OF THE INVENTION

The present invention relates to novel processes for preparing 2-quinoxalinecarboxylic acid and, more specifically, relates to the microbial oxidation of 2-methylquinoxaline to 2-quinoxalinecarboxylic acid.

BACKGROUND OF THE INVENTION

Methods are known in the art for microbial oxidation of certain aromatic heterocycles and, in particular, for microbial oxidation of methyl groups on certain aromatic heterocycles, such as, for example, those described in the following two articles: "Gene Order of the TOL Catabolic Plasmid Upper Pathway Operon and Oxidation of Both Toluene and Benzyl Alcohol by the xy/A Product," by S. Harayama et al., *J. Bacteriol.*, 167(2): 455–461 (1986) and "Enzymatic Oxidation of Methyl Groups on Aromatic Heterocycles: A Versatile Method for the Preparation of Heteroaromatic Carboxylic Acids," by A. Keiner, *Angew. Chem. Int. Ed. Engl.*, 31(6): 774–775 (1992).

U.S. Pat. No. 4,859,592 discloses a microbial process for the production of picolinic acid which can then be converted to pyridine products by chemical means.

U.S. Pat. Nos. 5,104,798; 5,213,973; and 5,236,832 disclose a microbial process for the oxidation of methyl groups in certain aromatic 5- or 6-member ring heterocycles to the corresponding carboxylic acids which is performed by a bacterium of the species Pseudomonas utilizing toluene, xylene or cymene as the inducer. As described therein, it is known in the art that the oxidation of the methyl group of toluene to benzoic acid by the strain *Pseudomonas putida* ATCC No. 33015 comprises three steps catalyzed by toluene monooxygenase, alcohol dehydrogenase and aldehyde dehydrogenase, respectively.

As described earlier with reference to the aforementioned article by Harayama et al., the TOL plasmid pWWO of *P. putida* mt-2 is a transmissible extrachromosomal element which encodes all of the enzymes required for the oxidative catabolism of several aromatic hydrocarbons, including toluene, m-xylene and p-xylene. Bacteria carrying TOL plasmids, e.g., *P. putida* ATCC No. 33015, can convert certain aromatic hydrocarbons to their corresponding aromatic carboxylic acids: both the xyl operon which codes for enzymes of xylene degradation and the genes which are responsible for the regulation of the xyl gene lie on the TOL plasmid pWWO. The genes on the TOL plasmid pWWO which code for the enzymes required for the above oxidations must be induced to produce such enzymes. Hence, the description of such induction in the aforementioned U.S. Pat. Nos. 5,104,798; 5,213,973; and 5,236,832.

As described in an article by Gaucher et al. in *Dev. Ind. Microbiol.*, 22: 219–232 (1981), the fungus *Penicillium griseofulvum* contains three enzymes for the conversion of m-cresol to m-hydroxybenzoic acid: m-cresol methyl hydroxylase, m-hydroxybenzyl alcohol dehydrogenase and m-hydroxybenzaldehyde hydroxylase.

To reiterate, as is known in the art, certain fungi and bacteria contain enzymes for the oxidation of methyl groups on certain aromatic rings to their corresponding carboxylic acids. While it is known then that methyl groups on such heteroaromatic rings can be oxidized to their corresponding carboxylic acids using microorganisms, as would be appreciated by those skilled in the art, the chemical and optical yields of such microbial oxidations generally vary substantially depending on, for example, the particular microorganism chosen, the concentration of the substrate, the structure of the substrate, and the like.

It has now been found that a range of microorganisms, including fungi and bacteria, substantially oxidize 2-methylquinoxaline to 2-quinoxalinecarboxylic acid. In addition, the subject process allows for suitable recovery of the 2-quinoxalinecarboxylic acid.

U.S. Provisional Patent Application No. 60/073,801 ("the '801 application") filed Feb. 5, 1998, now International PCT Application No. PCT/IB99/00067 filed Jan. 18, 1999, discloses the use of 2-quinoxalinecarboxylic acid as an intermediate in the synthesis of novel dihydroxyhexanoic acids which are useful to treat, e.g., inflammation and other immune disorders. The 2-quinoxalinecarboxylic acid provided by the novel processes of the present invention can be used to synthesize such dihydroxyhexanoic acids.

All of the documents cited herein, including the foregoing, are incorporated by reference herein in their entireties.

SUMMARY OF THE INVENTION

The present invention relates to a microbiological process for preparing 2-quinoxalinecarboxylic acid from 2-methylquinoxaline.

More particularly, the present invention relates to microbiological processes for preparing the compound of Formula I

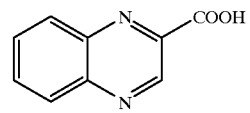

by contacting the compound of Formula II

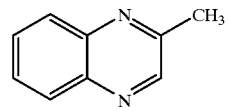

with a microorganism capable of accomplishing the oxidation of the methyl group of the compound of Formula II to the carboxyl group of the compound of Formula I, and incubating the resultant mixture under suitable conditions to yield an amount of the compound of Formula I.

Accordingly, the present invention provides processes for carrying out the microbial oxidation of the compound of Formula II, 2-methylquinoxaline, which comprises:

contacting the compound of Formula II with a microorganism, or a mutant thereof which is known or otherwise obtainable by those skilled in the relevant art and able, despite such mutation, to accomplish the subject oxidation ("a suitable mutant thereof"), and incubating the resulting mixture under conditions sufficient to yield an amount of the compound of Formula I, 2-quinoxalinecarboxylic acid, wherein said microorganism is selected from the group consisting of *Absidia glauca* ATCC No. 22752, *Absidia glauca* ATCC No. 74480, *Absidia pseudocylindrospora* ATCC No. 24169, *Absidia repens* ATCC No. 14849, *Absidia repens* ATCC No. 74481, *Actinomucor elegans* ATCC No. 6476, *Alternaria solani* ATCC No. 11078, *Aspergillus tamarii* ATCC No. 16865, *Coniophora puteana* ATCC No. 12675, *Cunninghamella echinulata* ATCC No. 8688a, *Cunninghamella echinulata* ATCC No. 8688b, *Cunninghamella echinulata* ATCC No. 8983, *Cunninghamella echinulata* ATCC No. 9244, *Cunninghamella echinulata* ATCC No. 9245, *Cunninghamella echinulata* ATCC No. 10028b, *Cunninghamella echinulata* ATCC No. 26269, *Cunninghamella echinulata* ATCC No. 36190, *Cunninghamella echinulata* ATCC No. 36112, *Cunninghamella homothallica* ATCC No. 16161, *Cylindrocarpon destructans* ATCC No. 66963, *Diplodia gossypina* ATCC No. 20575, *Epicoccum neglectum* ATCC No. 12723, *Glomerella lagenaria* ATCC No. 14724, *Penicillium claviforme* ATCC No. 10426, *Penicillium duclauxii* ATCC No. 10440, *Penicillium glabrum* ATCC No. 11080, *Pseudocochliobolus lunatus* ATCC No. 24155, *Pseudomonas putida* ATCC No. 33015, *Pseudomonas putida* ATCC No. 202190, *Rhodococcus rhodochrous* ATCC No. 19067 and *Thamnostylum piriforme* ATCC No. 8686; and suitable mutants thereof; provided that where said microorganism is said *Pseudomonas putida* ATCC No. 33015 or said *Pseudomonas putida* ATCC No. 202190, said *Pseudomonas putida* ATCC No. 33015 or said *Pseudomonas putida* ATCC No. 202190 is induced by interaction with an inducer prior to said contacting of said *Pseudomonas putida* ATCC No. 33015 or said *Pseudomonas putida* ATCC No. 202190 with said 2-methylquinoxaline.

The subject processes optionally further comprise the isolation of the desired product, 2-quinoxalinecarboxylic acid, by any suitable method. For example, the reaction mixture can be extracted with an organic solvent, preferably, ethyl acetate, and then the extracted material can be chromatographed. Alternatively, 2-quinoxalinecarboxylic acid can be adsorbed from the reaction mixture onto a resin, preferably a polymeric adsorbent resin, eluted therefrom using an organic solvent, preferably ethyl acetate, and crystallized from the eluted material using an organic solvent, or a combination of organic solvents, preferably ethyl acetate and methanol. Further yet, the 2-quinoxalinecarboxylic acid produced by the present processes may be treated with a suitable base, e.g., sodium hydroxide, resulting in the formation of a salt, e.g., sodium salt, of 2-quinoxalinecarboxylic acid. The alkali salt of 2-quinoxalinecarboxylic acid can then be isolated from the bioconversion medium by removal of the cells from the medium by filtration or centrifugation, followed by concentration of the cell-free medium, e.g., by evaporation.

The subject microorganism is preferably an intact microorganism.

In a preferred embodiment of the present invention the microorganism is a fungus.

In a preferred embodiment of the present invention wherein the microorganism is a fungus, the fungus is selected from the group consisting of the genera Absidia, Aspergillus, Alternaria, Penicillium, Diplodia and Cunninghamella.

In a particularly preferred embodiment of the present invention wherein the microorganism is a fungus, the fungus is of the genus Absidia. In an especially preferred embodiment of the present invention wherein the microorganism is a fungus of the genus Absidia, the microorganism is *A. glauca* ATCC No. 22752 or *A. glauca* ATCC No. 74480, or a suitable mutant thereof, or, further yet, any deposit of *A. glauca* ATCC No. 22752, or suitable mutant thereof, made to comply with the terms of the Budapest Treaty.

In another especially preferred embodiment of the present invention wherein the microorganism is a fungus of the genus Absidia, the microorganism is *A. repens* ATCC No. 14849 or *A. repens* ATCC No. 74481, or a suitable mutant thereof, or, further yet, any deposit of *A. repens* ATCC No. 14849, or a suitable mutant thereof, made to comply with the terms of the Budapest Treaty.

A preferred cell density for the fungal cultures of the present invention is from about 10 to about 30 g dry cell weight/L.

In another preferred embodiment of the present invention the microorganism is a bacterium.

In a preferred embodiment of the present invention wherein the microorganism is a bacterium, the bacterium is selected from the group consisting of the genera Pseudomonas and Rhodococcus.

In a particularly preferred embodiment of the present invention wherein the microorganism is a bacterium, the bacterium is of the genus Pseudomonas.

In an especially preferred embodiment of the present invention wherein the microorganism is a bacterium of the genus Pseudomonas, the microorganism is *P. putida* ATCC No. 33015 or *P. putida* ATCC No. 202190, or a suitable mutant thereof, or, further yet, any deposit of *P. putida* ATCC No. 33015, or suitable mutant thereof, made to comply with the terms of the Budapest Treaty.

A preferred cell density for the bacterial cultures of the present invention is a density which gives an optical density of from about 10 to about 30 at 650 nm.

As discussed above, in embodiments of the present invention wherein the microorganism is *P. putida* ATCC No. 33015 or *P. putida* ATCC No. 202190, or a suitable mutant thereof, the microorganism, or suitable mutant thereof, is induced prior to or during the contacting. It is preferred that the contacting occur after the completion of the induction of the microorganism. Preferred inducers include p-xylene and m-xylene. A particularly preferred inducer is p-xylene.

In a preferred embodiment of the present invention wherein the microorganism is *P. putida* ATCC No. 33015 or *P. putida* ATCC No. 202190, or a suitable mutant thereof, and the microorganism is cultured in a growth medium in a flask, the inducer is added to such growth medium prior to the contacting of the microorganism with 2-methylquinoxaline and incubated in such growth medium for a period of time sufficient for the substantial completion of such induction. The cells of the induced microorganism are collected by centrifuging the contents of the flask, removing, e.g., decanting, the spent growth medium (and thus the subject inducer), washing the cell pellet and resuspending the pellet in an aqueous medium, such as DPBS (Biowhittaker), prior to the contacting of said 2-methylquinoxaline with said microorganism.

In another preferred embodiment of the present invention wherein the microorganism is *P. putida* ATCC No. 33015 or *P. putida* ATCC No. 202190, or a suitable mutant thereof, and the subject microorganism is cultured in a growth medium in a fermentor, the inducer is continuously or continually added to such growth medium prior to the subject contacting of the microorganism with 2-methylquinoxaline and incubated in such growth medium for a period of time sufficient for the substantial completion of such induction, and then discontinued prior to the contacting of said 2-methylquinoxaline with said microorganism.

In a further preferred embodiment of the present invention the subject contacting is accomplished by adding 2-methylquinoxaline to a growth medium comprising the subject microorganism where the microorganism is a fungus. In a preferred embodiment of the present invention wherein the subject contacting is accomplished by adding 2-methylquinoxaline to a growth medium comprising the subject fungus, the growth medium is cornsteep solids medium. A particularly preferred cornsteep solids medium comprises from about 20 g to about 40 g/liter cornsteep solids and about 20 g/L dextrose, having a pH of about pH 4.85. Another preferred growth medium comprises about 20 g/L Pharmamedia® (Traders Protein) and about 20 g/L dextrose, having a pH of about pH 7.2.

In yet another preferred embodiment of the present invention the contactingis by adding the compound of Formula II adsorbed to a resin. See, for example, the article by J. T. Vicenzi et al., "Large-scale stereoselective enzymatic ketone reduction with in situ product removal via polymeric adsorbent resins," *Enzyme and Microbial Technology*, 20: 494–499 (1997).

In still another preferred embodiment of the present invention the contacting is accomplished by adding 2-methylquinoxaline to an aqueous medium comprising washed cells of the microorganism.

In yet another preferred embodiment of the present invention the microorganism is washed prior to the contacting of the microorganism with 2-methylquinoxaline. In a preferred embodiment of the present invention wherein the microorganism is washed prior to the contacting of the microorganism with 2-methylquinoxaline the washed microorganism is immobilized prior to the contacting.

In another preferred embodiment of the present invention the microorganism is grown in a cornsteep solids medium for from about twenty-four hours to about seventy-two hours prior to the contacting which is accomplished by adding 2-methylquinoxaline thereto.

The processes of the present invention further optionally comprise the isolation or separation of 2-quinoxalinecarboxylic acid, e.g., carried out by extraction with organic solvent, adsorption onto a resin, crystallization, or, as discussed above, where the alkali salt of 2-quinoxalinecarboxylic acid is provided, by concentration by evaporation of a cell-free medium, or the like.

The present invention further includes the use of 2-quinoxalinecarboxylic acid in the synthesis of the novel dihydroxyhexanoic acids disclosed in the aforementioned '801 application by following any of the methods disclosed in the '801 application or by using any other suitable methods therefor.

Those skilled in the art will fully understand the terms used herein to describe the present invention; nonetheless, the following terms used herein are as described immediately below.

"Intact microorganism" means that the cells of the microorganism substantially possess their inherent (and/or induced, as the case may be) mechanical, physical and biochemical integrities.

"Microbial oxidation" means the oxidation of the present invention as accomplished by the intact microorganism, or any preparation thereof, and the like.

"Microorganism" includes any intact microorganism or suitable preparation therefrom, including, for example, microorganism washed free of, e.g., fermentation medium, growth medium, culture broth, and the like, as the case may be; and microorganism immobilized, e.g., in a column, attached to beads, and the like.

DETAILED DESCRIPTION OF THE INVENTION

Unless otherwise noted, throughout this specification and the appendant claims:

° C. is degrees Centigrade;

% is percent;

ACN is acetonitrile;

DMSO is dimethylsulfoxide;

DPBS is Dulbeccos phosphate buffered saline;

EtOAC is ethyl acetate;

EtOH is ethanol;

g is gram;

HPLC is high performance liquid chromatography;

L is liter;

MeOH is methanol;

mg is milligram;

min is minute or minutes;

mm is millimeter;

mmol is millimoles;

mL is milliliter;

m-xylene is meta-xylene;

N is normal (concentration);

nM is nanomolar (concentration);

PBS is phosphate buffered saline;

p-xylene is para-xylene;

rpm is revolutions per minute;

TFA is trifluoroacetic acid;

$\mu$L is microliter;

v/v is volume per volume;

American National Can® is located in Menasha, Wis., U.S.A.;

Becton Dickinson® Labware is located in Franklin Lakes, N.J., U.S.A.;

Becton Dickinson® Microbiology Systems, Sparks, Md., U.S.A.;

Biowhittaker® is located in Walkersville, Md., U.S.A.;

Column Engineering®, Inc. is located in Ontario, Calif., U.S.A.;

IEC® Centrifuge is located in Needham Heights, Mass., U.S.A.;

Rohm and Haas® is located in Philadelphia, Pa., U.S.A.; and

Traders Protein® is located in Memphis, Tenn., U.S.A.

Further, ATCC is American Type Culture Collection which is located at 10801 University Boulevard, Manassas, Va., 20110–2209, U.S.A. TABLE 1 below lists the microorganisms disclosed herein and their depositor(s) (see, www.ATCC.com).

TABLE 1

| Fungal Culture, ATCC No. | Depositor |
|---|---|
| *Absidia glauca*, 22752 | NRRL[1] |
| *Absidia glauca*, 74480 | Pfizer Inc.[2] |
| *Absidia pseudocylindrospora*, 24169 | NRRL |

TABLE 1-continued

| | |
|---|---|
| Absidia repens, 14849 | NRRL |
| Absidia repens, 74481 | Pfizer Inc.[3] |
| Actinomucor elegans, 6476 | J. A. Stevenson |
| Alternaria solani, 11078 | P. W. Brian |
| Aspergillus tamarii, 16865 | K. B. Raper, D. I. Fennell |
| Coniophora puteana, 12675 | F. F. Lombard |
| Cunninghamella echinulata, 8688a | NRRL |
| Cunninghamella echinulata, 8688b | NRRL |
| Cunninghamella echinulata, 8983 | V. M. Cutter, Jr. |
| Cunninghamella echinulata, 9244 | V. M. Cutter, Jr. |
| Cunninghamella echinulata, 9245 | V. M. Cutter, Jr. |
| Cunninghamella echinulata, 10028b | NRRL |
| Cunninghamella echinulata, 26269 | J. J. Perry |
| Cunninghamella echinulata, 36190 | NRRL |
| Cunninghamella echinulata, 36112 | J. J. Perry |
| Cunninghamella homothallica, 16161 | IFO-Institute for Fermentation |
| Cylindrocarpon destructans, 66963 | G. J. Samuels |
| Diplodia gossypina, 20575 | Hoffman-La Roche Ltd. |
| Epicoccum neglectum, 12723 | Pfizer, Inc. |
| Glomerella lagenaria, 14724 | Sanraku-Ocean Co., Ltd. |
| Penicillium claviforme, 10426 | NRRL |
| Penicillium duclauxii, 10440 | NRRL |
| Penicillium glabrum, 11080 | P. W. Brian |
| Pseudocochliobolus lunatus, 24155 | R. S. Byther |
| Thamnostylum piriforme, 8686 | NRRL |

| Bacterial Culture, ATCC No. | Depositor |
|---|---|
| Pseudomonas putida, 33015 | P. A. Williams |
| Pseudomonas putida, 202190 | Pfizer Inc.[4] |
| R. rhodochrous, 19067 | J. W. Foster |

[1]NRRL is Northern Regional Research Laboratories (Peoria, Illinois).
[2]A. glauca, 22752, deposited under the terms of the Budapest Treaty on January 13, 1999.
[3]A. repens, 14849, deposited under the terms of the Budapest Treaty on January 13, 1999
[4]P. putida, 33015, deposited under the terms of the Budapest Treaty on January 13, 1999.

As discussed above, the present invention relates to microbiological processes for preparing the compound of Formula I

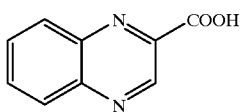

I by contacting the compound of Formula II

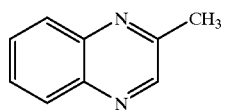

II with a microorganism capable of accomplishing the oxidation of the methyl group of Formula II, 2-methylquinoxaline, to the carboxyl group of Formula I, 2-quinoxalinecarboxylic acid, and incubating the resultant mixture under suitable conditions to yield), 2-quinoxalinecarboxylic acid.

The processes of the present invention are readily carried out. The microorganism is cultivated, with induction where necessary, e.g., where the microorganism is P. putida ATCC No. 33015 or P. putida ATCC No. 202190, or a suitable mutant thereof, and then contacted with 2-methylquinoxaline to oxidize the methyl group of 2-methylquinoxaline to the —COOH group of 2-quinoxalinecarboxylic acid. The 2-quinoxalinecarboxylic acid may then be, e.g., further reacted by methods described in the aforementioned '801 application to ultimately yield the novel dihydroxyhexanoic acids disclosed in the '801 application which are useful to treat inflammation and other immune disorders. The activity, methods for testing activities, dosages, dosage forms, methods of administration and background information concerning the novel dihydroxyhexanoic acids disclosed in the '801 application are set forth therein.

As discussed above, any suitable microorganism, or suitable mutant thereof, may be used in the processes of the present invention. As would be understood by those skilled in the art in light of the present disclosure, the conditions of the subject processes would be chosen depending upon, e.g., the kind of microorganism and the particular preparation thereof. For example, the pH, temperature, component concentrations, and the like, of the, e.g., fermentation medium and organic solvent, as well as the concentrations of 2-methylquinoxaline and the inducer (where employed) will be chosen to provide the particular desired result using the selected microorganism.

Preferred fungi include those members of the genera Absidia, Actinomucor, Alternaria, Aspergillus, Coniophora, Cunninghamella, Cylindrocarpon, Diplodia, Epicoccum, Fusarium, Glomerella, Penicillium, Pseudocochliobolus, Thamnostylum and Verticillium, but the species thereof is not particularly limitative provided that the microorganisms, or mutants thereof, are capable of accomplishing the subject oxidation.

Particularly preferred fungi belong to the genera Absidia, Alternaria, Aspergillus, Cunninghamella, Diplodia and Penicillium.

Especially preferred fungi belong to the genus Absidia.

More particularly, preferred fungi include A. glauca ATCC No. 22752, A. glauca ATCC No. 74480, A. pseudocylindrospora ATCC No. 24169, A. repens ATCC No. 14849, A. repens ATCC No. 74481, A. elegans ATCC No. 6476, A. solani ATCC No. 11078, A. tamarii ATCC No. 16865, C. puteana ATCC No. 12675, C. echinulata ATCC No. 8688a, C. echinulata ATCC No. 8688b, C. echinulata ATCC No. 8983, C. echinulata ATCC No. 9244, C. echinulata ATCC No. 9245, C. echinulata ATCC No. 10028b, C. echinulata ATCC No. 26269, C. echinulata ATCC No. 36190, C. echinulata ATCC No. 36112, C. homothallica ATCC No. 16161, C. destructans ATCC No. 66963, D. gossypina ATCC No. 20575, E. neglectum ATCC No. 12723 G. lagenaria ATCC No. 14724, P. claviforme ATCC No. 10426, P. duclauxii ATCC No. 10440, P. glabrum ATCC No. 11080, P. lunatus ATCC No. 24155 and T. piriforme ATCC No. 8686; and suitable mutants thereof.

More preferred fungi include A. glauca ATCC No. 22752, A. glauca ATCC No. 74480, A. repens ATCC No. 14849, A. repens ATCC No. 74481, A. solani ATCC No. 11078, A. tamarii ATCC No. 16865, C. echinulata ATCC No. 8983, D. gossypina ATCC No. 20575 and P. glabrum ATCC No. 11080; and suitable mutants thereof.

Particularly preferred fungi include A. glauca ATCC No. 22752, A. glauca ATCC No. 74480, A. repens ATCC No. 14849 and A. repens ATCC No. 74481; and suitable mutants thereof.

Especially preferred fungi include A. repens ATCC No. 14849 and A. repens ATCC No. 74481; and suitable mutants thereof.

Preferred bacteria include those belonging to the genera: Bacillus, Brevibacterium, Micrococcus, Pseudomonas and Rhodococcus, but the species thereof is not particularly limitative provided that the microorganisms, or mutants thereof, are capable of accomplishing the subject oxidation.

Particularly preferred bacteria include those belonging to the genera of Pseudomonas and Rhodococcus.

Especially preferred bacteria include those belonging to the genus Pseudomonas.

More particularly, preferred bacteria include *P. putida* ATCC No. 33015 *P. putida* ATCC No. 202190 and *R. rhodochrous* ATCC No.; and suitable mutants thereof.

Especially preferred bacteria are *P. putida* ATCC No. 33015 or *P. putida* ATCC No. 202190; and suitable mutants thereof.

As discussed earlier, the present invention includes the use of any suitable mutants of any of the suitable microorganisms. In addition, a group of mutants with more desirable properties, e.g., able to oxidize greater amounts of substrate, compared to the parent strain, can also be used in the subject process, and these new strains may be made using known methods including, for example, standard mutagenesis and selection techniques, and recombinant methods including, for example, site-directed mutagenesis.

Standard mutagenesis methods include chemical mutagenesis with N-methyl-N'-nitrosoguanidine (Delic et al. (1970), *Mutat. Res.* 9:167), nitrous acid (Crueger and Crueger (1984), *Biotechnology: A Textbook of Industrial Microbiology*, p. 16, Sinauer Associates, Inc., Sunderland, Mass., USA) and irradiation with ultraviolet light (Thrum (1984), in *Biotechnology of Industrial Antibiotics* (Vandamme, ed.), Marcel Dekker, New York, pp. 373–374).

Selection techniques include simple reisolation of the strain by the selection of an isolated colony, selection of specific colony morphologies and selection for resistance to analogues of components known or thought to be in the biosynthetic pathway of the compound of Formula I (Crueger and Crueger (1984), *Biotechnology: Textbook of Industrial Microbiology*, p. 24–25, Sinauer Associates, Inc., Sunderland, Mass., USA).

These new strains are used in the subject processes because, for example, they have improved properties relative to their respective parent strains, e.g., they produce more 2-quinoxalinecarboxylic acid, they exhibit less unwanted intrinsic degradative activity of 2-methylquinoxaline and/or 2-quinoxalinecarboxylic acid and/or the intermediate compounds which may be generated in the process of the present invention depending upon, for example, the particular microorganism chosen. In addition, where the mutant is utilized because its use results in more 2-quinoxalinecarboxylic acid, less volume of the culture needs to be grown to obtain the material necessary to generate an amount of 2-quinoxalinecarboxylic acid according to the present process which may result in substantial cost-savings.

As described earlier, any suitable preparation of the microorganism may be used in the processes of the present invention such as, for example, microorganism in growth medium, microorganism washed free of, e.g., fermentation medium, culture broth, and the like, or microorganism immobilized, e.g., in a column, attached to beads, and the like.

Those skilled in the art will understand from the description provided herein how to prepare suitable immobilized intact microorganism such as described, for example, by A. Bauer et al. in the article "Polyvinyl alcohol-immobilized whole-cell preparations for biotransformation of nitriles" published in *Biotechnology Letters*, 18(3): 343–348 (1996).

Preferred intact microorganisms will be those which substantially oxidize 2-methylquinoxaline to the product, specifically, 2-quinoxalinecarboxylic acid, while leaving the product substantially unaltered, e.g., free from intrinsic activity which might degrade or otherwise negatively impact the desired product at any stage of the subject processes.

The microorganisms suitable for use in the subject microbial oxidation may be prepared by any suitable method known to those skilled in the relevant art. An example of a suitable method for the preparation of a microorganism from a commercially purchased stock is provided below. Based upon the present disclosure including the methods provided below, those skilled in the art would understand how to modify any part of these methods, e.g., method of preparing the microorganism, free or immobilized; method of contacting of 2-quinoxalinecarboxylic acid with the microorganism; growth medium components and conditions, e.g., temperature, pH and the like; respective concentrations of 2-methylquinoxaline, inducer (where used); or incubation conditions; to achieve the desired result using any suitable microorganism.

In embodiments of the present invention wherein the microorganism is a fungus, a preferred concentration range of 2-methylquinoxaline is from about 0.01 g/L to about 2.5 g/L, and a particularly preferred range is from about 0.1 g/L to about 2.0 g/L. In embodiments of the present invention wherein the microorganism is a fungus selected from the group consisting of *A. repens* ATCC No. 14849, *A. repens* ATCC No. 74481, *A. glauca* ATCC No. 22752, *A. glauca* ATCC No. 74480 and suitable mutants thereof, a preferred concentration range of 2-methylquinoxaline is from about 0.1 g/L to about 2.0 g/L.

In embodiments of the present invention wherein the microorganism is a bacterium, a preferred concentration range of 2-methylquinoxaline is from about 0.01 g/L to about 1.5 g/L, and a particularly preferred range is from about 0.1 g/L to about 1.0 g/L. In embodiments of the present invention wherein the bacterium is selected from the group consisting of *P. putida* ATCC No. 33015, *P. putida* ATCC No. 202190 and suitable mutants thereof, a preferred concentration range of 2-methylquinoxaline is from about 0.1 g/L to about 1.0 g/L.

In addition, and as discussed earlier, bacterium carrying a TOL plasmid, e.g., *P. putida* ATCC No. 33015 or *P. putida* ATCC No. 202190, required for the subject oxidation, must be induced. In embodiments of the present invention wherein *P. putida* ATCC No. 33015 or *P. putida* ATCC No. 202190 is cultivated in a medium in a fermentor, the inducer, preferably p-xylene, is added at a preferred rate of addition of from about 4.5 mmol/L/hour to about 6.5 mmol/L/hour, and a particularly preferred rate of addition of from about 4.9 mmol/L/hour to about 6.1 mm/L/hour.

In embodiments of the present invention wherein *P. putida* ATCC No. 33015 or *P. putida* ATCC No. 202190 is in a medium in a flask, the inducer, preferably p-xylene, is added continuously in gaseous form to the medium. As would be understood by those skilled in the art from the present disclosure and from the aforementioned articles and patents (e.g., U.S. Pat. No. 5,236,832), the inducer concentration is usually selected so that it is lower than the minimal inhibitory concentration of the enzymes responsible for the oxidation. See also, Claus and Walker, *J. Gen. Microbiol.*, 36:107–122 (1964).

Any suitable method of contacting the substrate, 2-methylquinoxaline, with the microorganism may be used in the present invention. The substrate may be contacted with the microorganism in any suitable order. For example, 2-methylquinoxaline may be added to a medium, such as a culture broth, comprising the microorganism, free or immobilized, or some combination thereof; or the medium may comprise 2-methylquinoxaline and the microorganism may then be added to such medium; or 2-methylquinoxaline and the microorganism may be added together to such medium; or either 2-methylquinoxaline or the microorganism may be added to a suitable solvent comprising the other; or 2-methylquinoxaline may be adsorbed to a resin; and the like. Those skilled in the art will understand from the description provided herein how to modify any part of the subject processes as so desired.

As discussed above, it is preferred in the present invention that the microorganism is *A. glauca* ATCC No. 22752. As also discussed above, a lyophilized sample of *A. glauca* ATCC No. 22752 was deposited with the ATCC under the terms of the Budapest Treaty on Jan. 13, 1999. This newly deposited culture was given the new deposit number of ATCC No. 74480. Hence, it is also preferred in the present invention that the microorganism is *A. glauca* ATCC No. 74480. All restrictions on the availability to the public of the microorganism culture so deposited will be irrevocably removed upon the issuance of a patent from the specification of the present invention.

As also discussed above, it is especially preferred in the present invention that the microorganism is *A. repens* ATCC No. 14849. A lyophilized sample of *A. repens* ATCC No. 14849 was deposited with the ATCC under the terms of the Budapest Treaty on Jan. 13, 1999. This newly deposited culture was given the new deposit number of ATCC No. 74481. Hence, it is also especially preferred in the present invention that the microorganism is *A. repens* ATCC No. 74481. All restrictions on the availability to the public of the microorganism culture so deposited will be irrevocably removed upon the issuance of a patent from the specification of the present invention.

Cultures of the fungus *A. repens* ATCC No. 14849 (or *A. repens* ATCC No. 74481, *A. glauca* ATCC No. 22752, or *A. glauca* ATCC No. 74480) can be obtained from the ATCC, and an example of a suitable method for preparation from such an available stock is provided immediately below. Stock cultures can be prepared from rice cultures such as, for example, as follows: Erlenmeyer flasks (250 mL) containing about 50 g of brown rice and about 20 mL of distilled water are autoclaved at about 121° C. for about 30 min, a suspension of *A. repens* ATCC No. 14849 (or *A. repens* ATCC No. 74481, *A. glauca* ATCC No. 22752, or *A. glauca* ATCC No. 74480) vegetative cells, or spores, is prepared by adding either an aliquot of a liquid culture or a swab from a slant culture grown on agar medium to sterile distilled water. Each rice flask is inoculated with about 5 mL of the spore or cell suspension and incubated for about 10 days at about 28° C., at which time the spore stock is prepared by washing the rice culture with about a 0.5% solution of Tween 80 in distilled water, decanting the spore suspension away from the rice, and adding from about 10% to about 20% glycerol. The spore stock is stored at about −70° C.

As would be understood by those skilled in the art for any fungus selected, and as provided specifically hereinafter in the examples for the preferred *A. glauca* ATCC No. 22752 or ATCC No. 74480 and the especially preferred *A. repens* ATCC No. 14849 or ATCC No. 74481, a suitable method for preparing the selected fungus is as follows: the fungus is inoculated from the frozen vegetative cell or spore stock culture such as described above into a flask or a glass tube with a metal closure containing a growth medium (containing an aliquot from a sterile solution which includes Tween 80, glycerol and distilled water) whose composition is described in more detail below. The fermentation is carried out at temperatures ranging from about 22° C. to about 32° C., and preferably at about 29° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred pH range is from about pH 6 to about pH 7.

Any suitable duration of growth of the microorganism (i.e., fungus or bacterium), contacting of the microorganism with 2-methylquinoxaline, and incubation of 2-methylquinoxaline with the microorganism may be used in the present invention. Suitable growth of the microorganism may be achieved, e.g., within about 24 hours, at which time either (a) 2-methylquinoxaline itself, (b) a suitable aliquot of a solution of 2-methylquinoxaline in a suitable, e.g., does not undesirably affect the growth or function of the microorganism, solvent, preferably EtOH or (c) 2-methylquinoxaline adsorbed to a resin, may be added to the culture. The incubation may then be continued for, e.g., from about two to about twenty-four days, depending upon, for example, the vessel in which the bioconversion occurs, the medium and conditions, e.g., temperature, pH and agitation, of incubation. The incubation broth may then be extracted using any suitable extraction method, for example, (a) whereby a suitable solvent, such as, for example, EtOAc, methyl isobutylketone, methyl ethylketone, methylene chloride, and the like, preferably, EtOAc, removes the organic components from the incubation broth or (b) by adsorption of the product, 2-quinoxalinecarboxylic acid, onto a suitable resin, preferably a polymeric adsorbent resin, more preferably a resin selected from those of the tradename Amberlite® (Rohm and Haas), most preferably XAD4 (of the Amberlite resins). After extraction of the incubation broth with a suitable organic solvent and separation of the organic and aqueous phases, the compounds comprising the organic residue may be determined using any suitable method, such as, for example, chromatography. Alternatively, after extraction of 2-quinoxalinecarboxylic acid from the incubation broth using a resin, 2-quinoxalinecarboxylic acid can be eluted therefrom using a suitable solvent, preferably EtOAc or MeOH, and then crystallized from the, e.g., EtOAc, using, for example, EtOAc and MeOH.

Any suitable growth medium may be used in the process of the present invention, and the suitable growth medium will contain a source or sources of assimilable carbon, assimilable nitrogen and inorganic salts containing essential minerals. In general, many carbohydrates such as, for example, glucose, maltose, mannose, sucrose, starch, glycerin, millet jelly, molasses, soy bean, and the like, can be used as sources of assimilable carbon. Sources of assimilable nitrogen include, for example, materials such as yeast and casein hydrolysates, primary yeast, yeast extracts, cottonseed flour, soybean solids, wheat germ, meat extracts, peptone, cornsteep liquor, cornsteep solids, and ammonium salts. Suitable inorganic salt nutrients for use in the culture medium of the present invention include, for example, the customary salts containing sodium, iron, magnesium, potassium, cobalt, phosphate, and the like.

More particularly, components of growth media suitable for use in the present invention where the microorganism is a fungus include, for example, cornsteep liquor, cornsteep solids, Pharmamedia® and malt extract. Cornsteep liquor medium is prepared with about 40 g/L cornsteep liquor and about 20 g/L dextrose, and adjusted to about pH 4.85 before sterilization. Cornsteep solids medium is prepared with from about 20 g/L to about 40 g/L cornsteep solids and about 20 g/L dextrose, and adjusted to about pH 4.85 before sterilization. Another suitable medium for use in the processes of the present invention is prepared with about 20 g/L Pharmamedia® and about 20 g/L dextrose, and adjusted to about pH 7.2 before sterilization. Malt extract medium is prepared with about 10 g/L malt extract, about 10 g/L dextrose, about 5 g/L peptone, and about 2 g/L yeast extract, and adjusted to about pH 7 before sterilization. Another suitable medium for use in the processes of the present invention is prepared with about 20 g/L of dextrose, about 5 g/L of nutrisoy flour, about 5 g/L of yeast extract, about 5 g/L of NaCl and about 5 g/L of $K_2HPO_4$, with the pH adjusted to about pH 7.0 with $H_2SO_4$ before sterilization. A particularly preferred growth medium for the fungi suitable for the present process is the aforementioned cornsteep solids medium.

As discussed above, it is particularly preferred in the present invention that the microorganism is P. putida ATCC No. 33015. As also discussed above, a lyophilized sample of P. putida ATCC No. 33015 was deposited with the ATCC under the terms of the Budapest Treaty on Jan. 13, 1999. This newly deposited culture was given the new deposit number of ATCC No. 202190. Hence, it is also preferred in the present invention that the microorganism is P. putida ATCC No. 202190. All restrictions on the availability to the public of the microorganism culture so deposited will be irrevocably removed upon the issuance of a patent from the specification of the present invention.

In addition, growth media suitable for use in the present invention where the microorganism is a bacterium include any suitable known media, e.g., Nutrient Broth (about 32 g/L, Becton Dickinson Microbiology Systems) and glycerol (about 5 g/L). As would be understood by those skilled in the art for any bacterium selected, and as provided specifically hereinafter in the examples for P. putida ATCC No. 33015, a suitable method for preparing the selected bacterium is as follows: the bacteria is inoculated from a frozen stock culture prepared as is known in the art (about a 17% glycerol stock) into a flask or a glass tube with a metal closure or a fermentor containing a growth medium (containing an aliquot from a sterile solution which includes Tween 80, glycerol and distilled water) whose composition is described in more detail below. The fermentation is carried out at temperatures ranging from about 20° C. to about 40° C., and preferably at temperatures ranging from about 25° C. to about 32° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required. A preferred inoculum is from about 1% to about 20% v/v (inoculum/medium). A preferred pH range is from about pH 6 to about pH 8.

It should be noted that reference to particular buffers, media, reagents, contacting or culture conditions, amount of substrate, amount of inducer where used, and the like, in any part of the present disclosure is not intended to be limiting, but should be read to include all such related materials that those of ordinary skill in the art would recognize as being of interest or value in the particular context in which the discussion herein is presented. For example, it is often possible to substitute one buffer system or culture medium for another, such that a different but known way is used to achieve the same goals as those to which the use of a suggested method, material or composition is directed. Moreover, it should be understood that the present invention includes the scaling-up of the subject process for commercial purposes.

The subject microbial oxidation further optionally comprises the isolation of the desired product, 2-quinoxalinecarboxylic acid. The 2-quinoxalinecarboxylic acid may be isolated as described below from the medium in which the novel microbial oxidation process was performed and, more specifically, from any intermediate compounds which may have been produced but not completely converted to 2-quinoxalinecarboxylic acid depending upon, e.g., the microorganism selected and the conditions of incubation.

Any suitable methods for isolating and/or purifying any of the intermediates or the desired product of the subject process may be used in the present invention including filtration, extraction, crystallization, column chromatography, thin-layer chromatography, preparative low pressure liquid chromatography, HPLC, resin adsorption, or any suitable combination of such methods.

The detailed examples provided below show that a range of microorganisms, specifically, fungi and bacteria, oxidize 2-methylquinoxaline to yield 2-quinoxalinecarboxylic acid which may then be separated from any unwanted unaltered 2-methylquinoxaline, or any intermediate compounds, and further reacted according to methods well known in the art to yield, e.g., the compounds of the '801 application.

Although the present disclosure is primarily directed to the use of intact microorganisms in the subject processes, those skilled in the art would understand that the subject microbial processes may be accomplished by suitable preparations thereof, e.g., broken and dehydrated cell preparations, extracted materials comprising the microbial enzymes capable of accomplishing the subject oxidations, or the enzymes themselves, together with any necessary cofactors, and the like.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLE I

Oxidation of 2-Methylquinoxaline in Tube Cultures Using A. repens ATCC No. 14849

A. Bioconversion using the fungus A. repens ATCC No. 14849

Three "test" cultures (T1, T2 and T3) were prepared as follows about 2.5 mL of sterile growth medium (about 20 g/L of dextrose, about 5 g/L of nutrisoy flour, about 5 g/L of yeast extract, about 5 g/L of NaCl and about 5 g/L of $K_2HPO_4$, with the pH adjusted to about pH 7.0 with $H_2SO_4$ before sterilization) was added to each of three 16×125 mm glass tubes each having a metal closure (T1, T2 and T3), followed by the addition of spores (about 1% v/v of spore stock culture) of A. repens ATCC No. 14849 to T1, T2 and T3.

The three tube cultures were incubated at about 29° C., with shaking at about 210 rpm. After about 48 hours (T1), 72 hours (T2) or 96 hours (T3), about 0.05 mL of a stock solution (about 50 mg/mL in about 100% EtOH, final concentration of about 1 mg/mL) of 2-methylquinoxaline was added to the tube cultures.

After further incubation at about 29° C. (see TABLE 2 below), the fermentation broths of the tube cultures were adjusted to about pH 2 with 4N HCl. The contents of each tube culture were extracted with an equal volume of EtOAc (neat): the EtOAc was added, the tube culture was vortexed and then centrifuged at about 2,000 rpm (IEC Centrifuge). The EtOAc layer was removed and the aqueous layer extracted for a second time. The combined organic extracts were dried down, under nitrogen, in a water bath at about 50° C.

B. Yield of 2-quinoxalinecarboxylic Acid as Determined by Reverse-phase HPLC

Each of the extracts, prepared as described above, was resuspended in about one mL of ACN:water (1:9, v/v), and about 20 uL of each resuspended extract was analyzed by injection onto an HPLC column: Inertsil® C8 HPLC column (4.6×250 mm, Column Engineering, Inc.). The compounds contained within each injected resuspended extract were separated isocratically at about 1.0 mL per minute in a mobile phase (ACN:0.05% aqueous TFA, 1:4, v/v). Under these conditions, 2-quinoxalinecarboxylic acid eluted at about 8.6 min and 2-methylquinoxaline eluted at about 15 min. Yields of 2-quinoxalinecarboxylic acid were determined from such HPLC analysis for several sets of experimental conditions (i.e., T1, T2 and T3), and these yields are provided in TABLE 2 below.

TABLE 2

| Culture | Substrate addition time (days) | Initial substrate concentration (g/L) | Incubation time (days) | % Yield |
| --- | --- | --- | --- | --- |
| T1 | 2 | 1 | 18 | 56 |
| T2 | 3 | 1 | 14 | 76 |
| T3 | 4 | 1 | 16 | 79 |

As illustrated by the data for T1, T2 and T3 of TABLE 2, HPLC analysis shows that the subject microbial process results in 56%, 76% and 79% yields, respectively, of the desired 2-quinoxalinecarboxylic acid.

Accordingly, the inclusion of the intact microorganism, i.e., *A. repens* ATCC No. 14949, results in the oxidation of 2-methylquinoxaline to 2-quinoxalinecarboxylic acid, and a substantial amount of 2-quinoxalinecarboxylic acid remains intact.

EXAMPLE II

Oxidation of 2-Methylquinoxaline in Tube Cultures Using *A. repens* ATCC No. 14849 in Four Different Growth Media A. Preparation of Four Different Growth Media Medium 1 was prepared with about 40 g/L cornsteep liquor and about 20 g/L dextrose, and adjusted to about pH 4.85 before sterilization.

Medium 2 was prepared with about 40 g/L cornsteep solids and about 20 g/L dextrose, and adjusted to about pH 4.85 before sterilization.

Medium 3 was prepared with about 20 g/L Pharmamedia® and about 20 g/L dextrose, and adjusted to about pH 7.2 before sterilization.

Medium 4 was prepared with about 10 g/L malt extract, about 10 g/L dextrose, about 5 g/L peptone, and about 2 g/L yeast extract, and adjusted to about about pH 7 before sterilization.

B. Bioconversion Using the Fungus *A. repens* ATCC No. 14849

Eight "test" cultures (T1a, T1b, T2a, T2b, T3a, T3b, T4a and T4b) were prepared as follows: about 2.5 ml of sterile growth medium (Medium 1, Medium 2, Medium 3 and Medium 4, respectively) was added to each of eight 16×125 mm glass tubes each having a metal closure (T1a, T1b, T2a, T2b, T3a, T3b, T4a and T4b), followed by the addition of spores (about 1% v/v of spore stock culture) of *A. repens* ATCC No. 14849 to all of the tube cultures.

The eight tube cultures were incubated at about 29° C., with shaking at about 210 rpm. After about either 48 hours (T1a, T2a, T3a and T4a) or about 72 hours (T1b, T2b, T3b and T4b) about 0.05 mL of a stock solution (about 50 mg/mL in DMSO, final concentration of about 1 mg/mL) of 2-methylquinoxaline was added to the tube cultures.

After further incubation at about 29° C. for 12 days, the fermentation broth of each tube culture was extracted and the combined organic extracts dried down as described in EXAMPLE I.

C. Yield of 2-quinoxalinecarboxylic Acid as Determined by Reverse-phase HPLC

Each of the extracts, prepared as described above, was then processed for and analyzed by reverse phase HPLC as described in EXAMPLE I. Yields of 2-quinoxalinecarboxylic acid were determined from such HPLC analysis for several sets of experimental conditions (i.e., T1a, T1b, T2a, T2b, T3a, T3b, T4a and T4b), and these yields are provided in TABLE 3 below.

TABLE 3

| Medium | Culture | Substrate addition time (days) | % Yield |
| --- | --- | --- | --- |
| 1 | T1a | 2 | 36 |
|   | T1b | 3 | 43 |
| 2 | T2a | 2 | 73 |
|   | T2b | 3 | 69 |
| 3 | T3a | 2 | 49 |
|   | T3b | 3 | 52 |
| 4 | T4a | 2 | 31 |
|   | T4b | 3 | 28 |

As illustrated by the data of TABLE 3, HPLC analysis shows that the subject microbial process wherein the microorganism is *A. repens* ATCC No. 14849 results in the production of 2-quinoxalinecarboxylic acid in all of the media tested. The data of TABLE 3 also indicate that, of the four media tested, Medium 2 afforded the highest % yield of the desired product, 2-quinoxalinecarboxylic acid.

EXAMPLE III

Oxidation of 2-Methylquinoxaline in Flask Cultures Using *A. repens* ATCC No. 14849 or *A. glauca* ATCC No. 22752

A. Bioconversion using the fungus *A. repens* ATCC No. 14849 or the fungus *A. glauca* ATCC No. 22752.

Four "test" cultures (T1a, T1b, T2a and T2b) were prepared as follows: about 25 mL of sterile growth medium (about 20 g/L of dextrose, about 5 g/L of nutrisoy flour, about 5 g/L of yeast extract, about 5 g/L of NaCl and about 5 g/L of $K_2HPO_4$, with the pH adjusted to about pH 7.0 with $H_2SO_4$ before sterilization) was added to each of four conical flasks (300 mL), followed by the addition of spores (about 1% v/v of spore stock culture) of either *A. repens* ATCC No. 14849 (T1a, T1b) or *A. glauca* ATCC No. 22752 (T2a, T2b).

The four flask cultures were incubated at about 29° C., with shaking at about 210 rpm. Immediately after inoculation (T2a), or after about 24 hours (T2b), about 0.5 mL of a stock solution (about 50 mg/mL in about 100% EtOH, final concentration of about 1 mg/mL) of 2-methylquinoxaline was added to the flask cultures of *A. glauca* ATCC No. 22752, and after about 48 hours (T1a) or 72 hours (T1b), about 0.5 mL of a stock solution (about 50 mg/mL in about 100% EtOH, final concentration of about 1 mg/mL) of 2-methylquinoxaline was added to the flask cultures of *A. repens* ATCC No. 14849.

After further incubation at about 29° C. for 24 (T1a), 16 (T1b), 25 (T2a) or 24 (T2b) days, the fermentation broths of the flask cultures were adjusted to about pH 2 with 4N HCl. The contents of each flask culture were extracted with two 25 mL aliquots of EtOAc, and the solvent was removed from the combined EtOAc extracts under reduced pressure to yield the crude products.

B. Yield of 2-quinoxalinecarboxylic Acid as Determined by Reverse-phase HPLC

Each of the extracts, prepared as described above, was resuspended in about 5 mL of MeOH:ACN (3:2, v/v) and diluted 1:19 with water for HPLC analyses. HPLC analyses were performed as described for Example I. Yields of 2-quinoxaline carboxylic acid were determined from such HPLC analysis for several sets of experimental conditions (i.e., T1a, T1b, T2a and T2b), and these yields are provided in TABLE 4 below.

TABLE 4

| Culture | Substrate addition time (days) | Initial substrate concentration (g/L) | Incubation time (days) | % Yield |
| --- | --- | --- | --- | --- |
| T1a | 2 | 1 | 24 | 80 |
| T1b | 3 | 1 | 16 | 72 |
| T2a | 0 | 1 | 25 | 44 |
| T2b | 1 | 1 | 24 | 53 |

As illustrated by the data of TABLE 4, the inclusion of the intact microorganism, i.e., *A. glauca* ATCC No. 22752 or *A. repens* ATCC No. 14849, results in the oxidation of 2-methylquinoxaline to 2-quinoxalinecarboxylic acid. The % of the starting material, i.e., 2-methylquinoxaline, which remains in T1a, T1b, T2a and T2b is about 7%, 7%, 6% and 6%, respectively.

EXAMPLE IV

Screen for Microbial Conversion of 2-Methylquinoxaline to 2-Quinoxalinecarboxylic Acid Cells of various microorganisms were grown in the tubes containing 2.5 mL of the dextrose, nutrisoy flour medium as described in EXAMPLE I. Individual tubes were inoculated with spores or vegetative cells (about 1% v/v of spore or vegetative cell stock culture) of various microorganisms stored as frozen glycerol suspensions, and incubated at about 29° C. with agitation (210 rpm) on a rotary shaker. After about 48 hours, 0.05 mL of a 10 mg/mL solution of 2-methylquinoxaline in DMSO was added to each tube. After about 4 days incubation, the contents of each tube were extracted, and the individual extracts were analyzed by HPLC as described in EXAMPLE I. The yields of 2-quinoxalinecarboxylic acid were determined by HPLC and the results are summarized in TABLE 5.

TABLE 5

| Fungal Culture, ATCC No. | % Yield |
| --- | --- |
| A. glauca, 22752 | 83 |
| A. repens, 14849 | 83 |
| A. tamarii, 16865 | 53 |
| A. solani, 11078 | 53 |
| P. glabrum, 11080 | 47 |

TABLE 5-continued

| Fungal Culture, ATCC No. | % Yield |
| --- | --- |
| D. gossypina, 20575 | 31 |
| C. echinulata, 8983 | 25 |

EXAMPLE V

Oxidation of 2-Methylquinoxaline in Flask Cultures Using *P. putida* ATCC NO. 33015

Cells of *P. putida* ATCC No. 33015 were grown in Medium 5 (Nutrient Broth (about 32 g/L) and glycerol (about 5 g/L)). Six conical flasks (300 mL) containing about 30 mL of medium were inoculated with about 0.10 mL of a glycerol suspension of *P. putida* ATCC No. 33015 cells previously stored at about −70° C. After adding about 2 mL of p-xylene contained in a 15 mL conical polypropylene centrifuge tube (Falcon®, Becton Dickinson Labware) the flasks were sealed with Paraflim® (American National Can) and agitated (about 225 rpm) on a rotary shaker for about 18 hours at about 29° C. These flask cultures had an optical density of about 1.9 measured at 650 nm. Cells were collected from the six flasks by centrifugation, washed once with about 250 mL of DPBS, and resuspended in about 20 mL of PBS (Biowhittaker) in a 300 mL conical flask.

The bioconversion was started by addition of about 0.1 mL of about a 100 mg/mL solution of 2-methylquinoxaline in DMSO, corresponding to an initial concentration of about 0.5 g/L. Incubation was continued for about 4 days at about 29° C. with agitation at about 225 rpm. Samples of bioconversion broth were removed at various times and, after removal of cells by centrifugation, and dilution with MeOH as required, analyzed by HPLC. About 20 µL of each of these samples was analyzed by injection onto an Inertsil® HPLC C8 column (4.6×250 mm). Each column was eluted at about 1.0 mL/min with a mobile phase consisting of ACN:about 0.05% aqueous TFA (1:4, v/v). Yields of 2-quinoxalinecarboxylic acid were about 86%, 90%, and 94% after about 1, 2, and 4 days of incubation, respectively.

EXAMPLE VI

Oxidation of 2-Methylquinoxaline in a Fermentor Culture Using *P. putida* ATCC 33015

*P. putida* ATCC No. 33015 was grown in a fermentor with about 10 L of Medium 5. The fermentor was inoculated with six cultures of *P. putida* each grown in a conical flask (300 mL) containing about 50 mL of Medium 5. Each flask culture was inoculated with about 175 µL of a spore stock of *P. putida* ATCC 33015, a 15 mL polypropylene centrifuge tube containing about 2 mL of p-xylene was inserted, and the flask sealed with Parafilm®. These flask cultures were incubated at about 29° C. for about 17 hours with shaking at about 210 rpm. After inoculation of the fermentor with the 6 flask cultures, p-xylene was added to the fermentor in about 2 mL aliquots about every 20 min for 2 hours. Thereafter, about 2.5 mL aliquots of p-xylene were added to the fermentor about every 20 min for about 3.5 hours. Xylene addition was then discontinued and 2-methylquinoxaline was added at about 5.25 hours (about 1.95 g) and about 7.75 hours (about 7.76 g) after inoculation. Incubation was continued for about 22 hours after the final 2-methylquinoxaline addition. A sample of the incubation medium was centrifuged to remove the cells, diluted with MeOH and analyzed by HPLC using the method described in EXAMPLE V. This analysis revealed about an 81% yield of 2-quinoxalinecarboxylic acid.

What is claimed is:

1. A process for the microbial oxidation of 2-methylquinoxaline to 2-quinoxalinecarboxylic acid which comprises contacting said 2-methylquinoxaline with a microorganism and incubating the resulting mixture under conditions sufficient to yield an amount of said 2-quinoxalinecarboxylic acid, wherein said microorganism is selected from the group consisting of *Absidia glauca* ATCC No. 74480, *Absidia pseudocylindrospora* ATCC No. 24169, *Absidia repens* ATCC No. 74481, *Actinomucor elegans* ATCC No. 6476, *Alternaria solani* ATCC No. 11078, *Aspergillus tamarii* ATCC No. 16865, *Coniophora puteana* ATCC No. 12675, *Cunninghamella echinulata* ATCC No. 8688a, *Cunninghamella echinulata* ATCC No. 8688b, *Cunninghamella echinulata* ATCC No. 8983, *Cunninghamella echinulata* ATCC No. 9244, *Cunninghamella echinulata* ATCC No. 9245, *Cunninghamella echinulata* ATCC No. 10028b, *Cunninghamella echinulata* ATCC No. 26269, *Cunninghamella echinulata* ATCC No. 36190, *Cunninghamella echinulata* ATCC No. 36112, *Cunninghamella homothallica* ATCC No. 16161, *Cylindrocarpon destructans* ATCC No. 66963, *Diplodia gossypina* ATCC No. 20575, *Epicoccum neglectum* ATCC No. 12723, *Glomerella lagenaria* ATCC No. 14724, *Penicillium claviforme* ATCC No. 10426, *Penicillium duclauxii* ATCC No. 10440, *Penicillium glabrum* ATCC No. 11080, *Pseudocochliobolus lunatus* ATCC No. 24155, *Pseudomonas putida* ATCC No. 33015, *Pseudomonas putida* ATCC No. 202190, *Rhodococcus rhodochrous* ATCC No. 19067 and *Thamnostylum piriforme* ATCC No. 8686; and suitable mutants thereof; provided that where said microorganism is said *Pseudomonas putida* ATCC No. 202190, said *Pseudomonas putida* ATCC No. 202190 is induced by interaction with an inducer prior to said contacting of said *Pseudomonas putida* ATCC No. 202190 with said 2-methylquinoxaline.

2. The process as defined in claim 1 further comprising isolating 2-quinoxalinecarboxylic acid.

3. The process as defined in claim 2 wherein said isolation is carried out by extraction of said mixture with an organic solvent.

4. The process as defined in claim 3 wherein said organic solvent is ethyl acetate.

5. The process as defined in claim 4 further comprising subjecting said extraction to chromatography.

6. The process as defined in claim 2 wherein said isolation is carried out by adsorption of said 2-quinoxalinecarboxylic acid from said mixture onto a resin and elution of said adsorbed 2-quinoxalinecarboxylic acid from said resin with an organic solvent.

7. The process as defined in claim 6 wherein said resin is a polymeric adsorbent resin.

8. The process as defined in claim 7 wherein said organic solvent is ethyl acetate or methanol.

9. The process as defined in claim 8 further comprising crystallizing said eluted 2-quinoxalinecarboxylic acid from ethyl acetate.

10. The process as defined in claim 8 further comprising crystallizing said eluted 2-quinoxalinecarboxylic acid from ethyl acetate and methanol.

11. The process as defined in claim 1 wherein said microorganism is an intact microorganism.

12. The process as defined in claim 11 wherein said microorganism comprises washed cells of said microorganism.

13. The process as defined in claim 12 further comprising immobilizing said washed cells.

14. The process as defined in claim 12 wherein said washed cells are in an aqueous solvent.

15. The process as defined in claim 14 wherein said contacting is by adding said 2-methylquinoxaline to said solvent.

16. The process as defined in claim 11 wherein said microorganism is in a growth medium.

17. The process as defined in claim 16 wherein said contacting is by adding said 2-methylquinoxaline to said growth medium.

18. The process as defined in claim 1 wherein said microorganism is selected from the group consisting of said *Absidia glauca* ATCC No. 74480, *Absidia repens* ATCC No. 74481, *Alternaria solani* ATCC No. 11078, *Aspergillus tamarii* ATCC No. 16865, *Cunninghamella echinulata* ATCC No. 8983 and *Diplodia gossypina* ATCC No. 20575; and said mutants thereof.

19. The process as defined in claim 18 wherein said microorganism is selected from the group consisting of said *Absidia glauca* ATCC No. 74480, *Absidia repens* ATCC No. 74481, *Alternaria solani* ATCC No. 11078 and *Aspergillus tamarii* ATCC No. 16865; and said mutants thereof.

20. The process as defined in claim 19 wherein said microorganism is selected from the group consisting of said *Absidia glauca* ATCC No. 74480 and *Absidia repens* ATCC No. 74481; and said mutants thereof.

21. The process as defined in claim 20 wherein said microorganism is *Absidia repens* ATCC No. 74481.

22. A process for the microbial oxidation of 2-methylquinoxaline to 2-quinoxalinecarboxylic acid which comprises contacting said 2-methylquinoxaline with a microorganism and incubating the resulting mixture under conditions sufficient to yield an amount of said 2-quinoxalinecarboxylic acid, wherein said microorganism is *Absidia repens* ATCC No. 74481; and suitable mutants thereof.

23. The process as defined in claim 22 wherein said microorganism is in a growth medium.

24. The process as defined in claim 23 wherein said contacting is by adding said 2-methylquinoxaline to said growth medium.

25. The process as defined in claim 1 wherein said microorganism is said *Pseudomonas putida* ATCC No. 202190.

26. The process as defined in claim 25 wherein said inducer is p-xylene.

27. The process as defined in claim 26 wherein said *Pseudomonas putida* ATCC No. 202190 is in a growth medium.

28. The process as defined in claim 27 wherein said p-xylene is added to said growth medium.

29. The process as defined in claim 28 wherein said growth medium is in a flask.

30. The process defined in claim 29 further comprising the step of collecting said microorganism after completion of said induction.

31. The process as defined in claim 30 wherein said collecting is by centrifuging the contents of said flask, decanting the fluid, washing the cell pellet and resuspending said pellet in a buffer.

32. The process as defined in claim 31 wherein said contacting is by adding said 2-methylquinoxaline to said buffer after said resuspension.

33. The process as defined in claim 28 wherein said growth medium is in a fermentor.

34. The process as defined in claim 33 wherein said addition of said p-xylene to said growth medium is discontinued after said induction.

35. The process as defined in claim 34 wherein said contacting is by adding said 2-methylquinoxaline to said growth medium after said discontinuation of said p-xylene.

36. A process for the microbial oxidation of 2-methylquinoxaline to 2-quinoxalinecarboxylic acid which comprises contacting 2-methylquinoxaline with a microorganism after the enzymes of said microorganism are induced by interaction with an inducer and incubating the resulting mixture under conditions sufficient to yield an amount of said 2-quinoxalinecarboxylic acid, wherein said microorganism is *Pseudomonas putida* ATCC No. 202190; or suitable mutants thereof.

37. The process as defined in claim 36 wherein said inducer is p-xylene or m-xylene.

\* \* \* \* \*